US 7,438,875 B2

(12) United States Patent
Do et al.

(10) Patent No.: US 7,438,875 B2
(45) Date of Patent: Oct. 21, 2008

(54) METHOD FOR REDUCING ODOR USING METAL-MODIFIED SILICA PARTICLES

(75) Inventors: Bao Trong Do, Decatur, GA (US); John Gavin MacDonald, Decatur, GA (US); Jaeho Kim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 488 days.

(21) Appl. No.: 10/686,938

(22) Filed: Oct. 16, 2003

(65) Prior Publication Data

US 2005/0084438 A1    Apr. 21, 2005

(51) Int. Cl.
B01D 47/00    (2006.01)
(52) U.S. Cl. ......................... 423/210; 502/406
(58) Field of Classification Search .............. 423/210; 502/406, 407, 243, 244, 245, 253, 241, 242, 502/247, 248, 256, 257, 258, 259, 260
See application file for complete search history.

(56) References Cited

U.S. PATENT DOCUMENTS

| | | | |
|---|---|---|---|
| 2,015,864 A | 10/1935 | Müller et al. |
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A | 4/1970 | Berry |
| 3,542,615 A | 11/1970 | Dobo et al. |
| 3,615,478 A | 10/1971 | Hoshino et al. |
| 3,692,618 A | 9/1972 | Dorschner et al. |
| 3,794,497 A | 2/1974 | Pratt et al. |
| 3,802,817 A | 4/1974 | Matsuki et al. |
| 3,836,633 A | 9/1974 | Beschke |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,451,388 A | 5/1984 | Payne |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Hagiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |

(Continued)

FOREIGN PATENT DOCUMENTS

EP    0103214 B1    3/1984

(Continued)

OTHER PUBLICATIONS

Abstract of Japanese Patent No. JP04255767, Sep. 10, 1992.

(Continued)

Primary Examiner—Edward M Johnson
(74) Attorney, Agent, or Firm—Dority & Manning, P.A.

(57) ABSTRACT

A method for reducing odor is provided. In one embodiment, the method comprises modifying the surface of silica particles with a transition metal so that the silica particles are bonded to the transition metal through a covalent or coordinate bond. The method further comprises contacting the modified silica particles with an odorous compound, the transition metal facilitating the capture of the odorous compound.

36 Claims, No Drawings

U.S. PATENT DOCUMENTS

| | | |
|---|---|---|
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,064,599 A | 11/1991 | Ando et al. |
| 5,100,581 A | 3/1992 | Watanabe et al. |
| 5,100,702 A | 3/1992 | Maeda et al. |
| 5,102,592 A | 4/1992 | McCauley et al. |
| 5,108,739 A | 4/1992 | Kurihara et al. |
| 5,120,693 A | 6/1992 | Connolly et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,314,855 A | 5/1994 | Thorpe et al. |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,380,510 A * | 1/1995 | Matsui et al. ................ 423/338 |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,432,000 A | 7/1995 | Young, Sr. et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,500,209 A * | 3/1996 | Mendolia et al. .............. 424/66 |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,614,570 A * | 3/1997 | Hansen et al. ................. 524/13 |
| 5,616,315 A | 4/1997 | Masterman et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,858,503 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,998,222 A | 12/1999 | Weimer |
| 6,004,625 A | 12/1999 | Oshima |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,111,010 A * | 8/2000 | Yu et al. ..................... 524/588 |
| 6,111,163 A | 8/2000 | McCormack et al. |
| 6,177,608 B1 | 1/2001 | Weinstrauch |
| 6,193,844 B1 | 2/2001 | McLaughlin et al. |
| 6,200,555 B1 | 3/2001 | Nishijima et al. |
| 6,210,625 B1 | 4/2001 | Matsushita et al. |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,489 B1 | 8/2001 | Abbott et al. |
| 6,277,772 B1 | 8/2001 | Gancet et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,344,218 B1 | 2/2002 | Dodd et al. |
| 6,358,909 B1 | 3/2002 | Ochomogo et al. |
| 6,361,780 B1 | 3/2002 | Ley et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,410,616 B1 | 6/2002 | Harada et al. |
| 6,410,765 B1 | 6/2002 | Wellinghoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,432,872 B1 | 8/2002 | Tsushio et al. |
| 6,433,243 B1 | 8/2002 | Woltman et al. |
| 6,440,187 B1 | 8/2002 | Kasai et al. |
| 6,460,989 B1 | 10/2002 | Yano et al. |

| | | | | | | |
|---|---|---|---|---|---|---|
| 6,461,735 B1 | 10/2002 | Furuya et al. | EP | 0972563 A1 | 1/2000 | |
| 6,467,897 B1 | 10/2002 | Wu et al. | EP | 1034800 A1 | 9/2000 | |
| 6,468,500 B1 | 10/2002 | Sakaguchi et al. | EP | 1157672 A1 | 11/2001 | |
| 6,475,601 B1 | 11/2002 | Sakaki et al. | EP | 1162172 A1 | 12/2001 | |
| 6,479,150 B1 | 11/2002 | Liu et al. | EP | 1188854 A1 | 3/2002 | |
| 6,491,790 B1 | 12/2002 | Proverb et al. | EP | 1214878 A1 | 6/2002 | |
| 6,498,000 B2 | 12/2002 | Murasawa et al. | EP | 1216675 A1 | 6/2002 | |
| 6,517,199 B1 | 2/2003 | Tomioka et al. | EP | 1298071 A1 | 4/2003 | |
| 6,531,704 B2 | 3/2003 | Yadav et al. | EP | 1315526 B1 | 6/2003 | |
| 6,536,890 B1 | 3/2003 | Kato et al. | EP | 1053788 B1 | 10/2003 | |
| 6,548,264 B1 | 4/2003 | Tan et al. | JP | 62149322 | 7/1987 | |
| 6,551,457 B2 | 4/2003 | Westman et al. | JP | 3221142 | 9/1991 | |
| 6,562,441 B1 | 5/2003 | Maeda et al. | WO | WO 8902698 A1 | 4/1989 | |
| 6,575,383 B2 | 6/2003 | Dobler et al. | WO | WO 9111977 A1 | 8/1991 | |
| 6,578,521 B2 | 6/2003 | Raymond et al. | WO | WO 9112029 A1 | 8/1991 | |
| 6,589,562 B1 | 7/2003 | Shefer et al. | WO | WO 9112030 A1 | 8/1991 | |
| 6,607,711 B2 | 8/2003 | Pedersen | WO | WO 9619346 A2 | 6/1996 | |
| 6,623,848 B2 | 9/2003 | Brehm et al. | WO | WO 9619346 A3 | 6/1996 | |
| 6,638,918 B2 | 10/2003 | Davison et al. | WO | WO 9725076 A1 | 7/1997 | |
| 6,639,004 B2 | 10/2003 | Falat et al. | WO | WO 9820915 A1 | 5/1998 | |
| 6,645,569 B2 | 11/2003 | Cramer et al. | WO | WO 9826808 A2 | 6/1998 | |
| 6,693,071 B2 | 2/2004 | Ghosh et al. | WO | WO 9826808 A3 | 6/1998 | |
| 7,008,979 B2 | 3/2006 | Schottman et al. | WO | WO 9947252 A3 | 9/1999 | |
| 2001/0000889 A1 | 5/2001 | Yadav et al. | WO | WO 0003797 A1 | 1/2000 | |
| 2001/0023338 A1 | 9/2001 | Guarracino et al. | WO | WO 00/13764 A1 | 3/2000 | |
| 2001/0031248 A1 | 10/2001 | Hall-Puzio et al. | WO | WO 0029036 A2 | 3/2000 | |
| 2001/0056246 A1 | 12/2001 | Rodriguez-Fernandez | WO | WO 0059555 A1 | 10/2000 | |
| 2002/0005145 A1 | 1/2002 | Sherman | WO | WO 0076558 A1 | 12/2000 | |
| 2002/0066542 A1 | 6/2002 | Jakob et al. | WO | WO 0106054 A1 | 1/2001 | |
| 2002/0091071 A1 | 7/2002 | Fischer et al. | WO | WO 0226272 A1 | 4/2002 | |
| 2002/0106466 A1 | 8/2002 | Hausmann et al. | WO | WO 0249559 A2 | 6/2002 | |
| 2002/0110686 A1 | 8/2002 | Dugan | WO | WO 02055115 A1 | 7/2002 | |
| 2002/0128336 A1 | 9/2002 | Kolb et al. | WO | WO 02062881 A2 | 8/2002 | |
| 2002/0142937 A1 | 10/2002 | Carter et al. | WO | WO 02064877 A2 | 8/2002 | |
| 2002/0149656 A1 | 10/2002 | Nohr et al. | WO | WO 02064877 A3 | 8/2002 | |
| 2002/0150678 A1 | 10/2002 | Cramer et al. | WO | WO 02083297 A1 | 10/2002 | |
| 2002/0176982 A1 | 11/2002 | Rohrbaugh et al. | WO | WO 02084017 A1 | 10/2002 | |
| 2002/0177621 A1 | 11/2002 | Hanada | WO | WO 02094329 A1 | 11/2002 | |
| 2002/0182102 A1 | 12/2002 | Fontenot et al. | WO | WO 02095112 A1 | 11/2002 | |
| 2003/0013369 A1 | 1/2003 | Soane et al. | WO | WO 03000979 A2 | 1/2003 | |
| 2003/0021983 A1 | 1/2003 | Nohr et al. | WO | WO 03025067 A1 | 3/2003 | |
| 2003/0050211 A1 | 3/2003 | Hage et al. | WO | WO 03032959 A1 | 4/2003 | |
| 2003/0056648 A1 | 3/2003 | Fornai et al. | WO | WO 03088931 | 10/2003 | |
| 2003/0070782 A1 | 4/2003 | Proverb et al. | WO | WO 03092885 A1 | 11/2003 | |
| 2003/0082237 A1 | 5/2003 | Cha et al. | WO | WO 2004000986 A1 | 12/2003 | |
| 2003/0099718 A1 | 5/2003 | Burrell et al. | WO | WO 060378 A2 | 7/2004 | |
| 2003/0100842 A1 | 5/2003 | Rosenberg et al. | | | | |
| 2003/0147956 A1 | 8/2003 | Shefer et al. | | | | |
| 2003/0147966 A1 | 8/2003 | Franzen et al. | | | | |
| 2003/0181540 A1 | 9/2003 | Quellet et al. | | | | |
| 2003/0203009 A1 | 10/2003 | MacDonald | | | | |
| 2003/0235605 A1 | 12/2003 | Lelah et al. | | | | |
| 2004/0033269 A1 | 2/2004 | Hei et al. | | | | |
| 2004/0034157 A1 | 2/2004 | Ghosh et al. | | | | |
| 2004/0043688 A1 | 3/2004 | Soerens et al. | | | | |
| 2004/0122387 A1 | 6/2004 | Long et al. | | | | |
| 2005/0181067 A1 | 8/2005 | Yokoyama et al. | | | | |

FOREIGN PATENT DOCUMENTS

| | | |
|---|---|---|
| EP | 0232141 A1 | 8/1987 |
| EP | 0251783 B1 | 1/1988 |
| EP | 0282287 B2 | 9/1988 |
| EP | 0339461 B1 | 11/1989 |
| EP | 0348978 A2 | 1/1990 |
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |

OTHER PUBLICATIONS

Abstract of Japanese Patent No. JP05098185, Apr. 20, 1993.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Article—*Immunization of mice with peptomers covalently coupled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
PCT Search Report for PCT/US03/32846, Jun. 7, 2004.
Abstract of Japanese Patent No. 7256025, Oct. 9, 1995.
Abstract of Japanese Patent No. 5106199, Apr. 27, 1993.
Abstract of Japanese Patent No. 9143872, Jun. 3, 1997.

Article—*Applicability of a SPME method for the Rapid Determination of VOCs*, Alexandre Béné, Jean-Luc Luisier, and Antoine Fornage, Chimia, vol. 56, No. 6, 2002, pp. 289-291.

Article—*Characterisation of novel modified active carbons and marine algal biomass for the selective adsorption of lead*, D.J. Malik, V. Strelko, Jr., M. Streat, and A.M. Puziy, Water Research, vol. 36, 2002, pp. 1527-1538.

Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.

Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.

Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.

Article—*Validation of $^{13}C$-Urea Breath Test for the Diagnosis of Helicobacter pylori Infection in the Singapore Population*, T. S. Chua, K. M. Fock, E. K. Teo, T. M. Ng, Singapore Medical Journal, vol. 43, No. 8, 2002, pp. 408-411.

Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.

Article—*Spectrophotometric Assay of Thiols*, Peter C. Jocelyn, Methods in Enzymology, vol. 142, 1987, pp. 44-67.

Article—*Adsorption of Dyes on Nanosize Modified Silica Particles*, Guangwei, Wu, Athanasia Koliadima, Yie-Shein Her, and Egon Matijevic, Journal of Colloid and Interface Sciences, vol. 195, 1997, pp. 222-228.

Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.

Article—*Saponins and Sapogenins. VIII. Surface Films of Echinocystic Acid and Derivatives*, C. R. Noller, J. Am. Chem. Soc., vol. 60, 1938, 3 pages.

Article—*Synthesis of porous Silica with help from cyclodextrin aggregates*, Markus Antonietti, Max-Planck-Institut für Kolloidund, Germany, 1 page.

Article—*Immobilization of $(n-Bu_4N)_4W_{10}O_{32}$ on Mesoporous MCM-41 and Amorphous Silicas for Photocatalytic Oxidation of Cycloalkanes with Molecular Oxygen*, Andrea Maldotti, Alessandra Molinari, Graziano Varani, Maurizio Lenarda, Loretta Storaro, Franca Bigi, Raimondo Maggi, Alessandro Mazzacani, and Giovanni Sartori, Journal of Catalysis, vol. 209, 2002, pp. 210-216.

Article—*Fe-MCM-41 for Selective Epoxidation of Styrene with Hydrogen Peroxide*, Qinghong Zhang, Ye Wang, Satoko Itsuki, Tetsuya Shishido, and Katsuomi Takehira, The Chemical Society of Japan, Chemistry Letters 2001, pp. 946-947.

Article—*Mesoporous Sieves with Unified Hybrid Inorganic/Organic Frameworks*, Brian J. Melde, Brian T. Holland, Christopher F. Blanford, and Andreas Stein, Chem. Mater., vol. 11, No. 11, 1999, pp. 3302-3308.

Article—*From Cyclodextrin Assemblies to Porous Materials by Silica Templating*, Sebastian Polarz, Bernd Smarsly, Lyudmila Bronstein, and Markus Antonietti, Angew. Chem. Int., vol. 40, No. 23, 2001, pp. 4417-4421.

Paper—*Uniform Deposition of Ultrathin Polymer Films on the Surfaces of $Al_2O_3$ Nanoparticles by a Plasma Treatment*, Donglu Shi, S. X. Wang, Wim J. van Ooij, L. M. Wang, Jiangang Zhao, and Zhou Yu, University of Cincinnati and University of Michigan, Jun. 2000.

Article—*Nanoparticles based on polyelectrolyte complexes: effect of structure and net charge on the sorption capability for solved organic molecules*, H.-M. Buchhammer, G. Petzold, and K. Lunkwitz, Colloid Polym. Sci., vol. 278, 2000, pp. 841-847.

Article—*Asorption of Gases in Multimolecular Layers*, Stephen Brunauer, P.H. Emmett, and Edward Teller, The Journal of the American Chemical Society, vol. 60, Feb. 1938, pp. 309-319.

U.S. Appl. No. 10/325,474, filed Dec. 20, 2002, Lye, et al., Delivery System For Functional Compounds.

U.S. Appl. No. 10/328,730, filed Dec. 23, 2002, Quincy, III, et al., Odor Control Composition.

U.S. Appl. No. 10/686,933, filed Oct. 16, 2003, MacDonald, et al., Method For Reducing Odor Using Colloidal Nanoparticles.

U.S. Appl. No. 10/686,937, filed Oct. 16, 2003, Wu, et al., Method For Reducing Odor Using Coordinated Polydentate Compounds.

U.S. Appl. No. 10/686,939, filed Oct. 16, 2003, McGrath, et al., Method For Reducing Odor Using Metal-Modified Particles.

U.S. Appl. No. 10/686,687, filed Oct. 16, 2003, MacDonald, et al., Durable Charged Particle Coatings And Materials.

U.S. Appl. No. 10/687,004, filed Oct. 16, 2003, Urlaub, et al., High Surface Area Material Blends For Odor Reduction, Articles Utilizing Such Blends And Methods Of Using Same.

U.S. Appl. No. 10/687,269, filed Oct. 16, 2003, MacDonald, et al., Odor Controlling Article Including A Visual Indicating Device For Monitoring Odor Absorption.

U.S. Appl. No. 10/687,270, filed Oct. 16, 2003, MacDonald, et al., Visual Indicating Device For Bad Breath.

U.S. Appl. No. 10/687,327, filed Oct. 16, 2003, Boga, et al., Method And Device For Detecting Ammonia Odors And *Helicobacter pylori* Urease Infection.

U.S. Appl. No. 10/687,425, filed Oct. 16, 2003, Fish, et al., Odor Absorbing Extrudates.

\* cited by examiner

METHOD FOR REDUCING ODOR USING METAL-MODIFIED SILICA PARTICLES

BACKGROUND OF THE INVENTION

Odor control additives have been conventionally incorporated into substrates for a variety of reasons. For instance, U.S. Pat. No. 6,225,524 to Guarracino, et al. describes a substrate having an odor control composition that includes an absorbent gelling material and silica. Likewise, U.S. Pat. No. 6,376,741 to Guarracino, et al. describes a substrate having an odor control composition that includes silica and a zeolite (i.e., crystalline aluminosilicate). For instance, one type of silica said to be preferred in Guarracino, et al. ('524 patent) is amorphous silica having a particle size of 4-12 microns and a pore volume of 1-2 g/ml. Another type of preferred silica is said to be a silica gel having a medium pore diameter of from 90 to 110 angstroms, a surface area of from 250 $m^2/g$ to 350 $m^2/g$, and an average particle size of from 63 to 200 microns. Unfortunately, conventional odor control compositions, such as described above, have proven ineffective in obtaining the full level of odor control desired in many applications.

As such, a need exists for an odor control composition that may exhibit improved odor control properties, particularly when applied to a substrate.

SUMMARY OF THE INVENTION

In accordance with one embodiment of the present invention, a method for reducing odor is disclosed. The method comprises modifying the surface of silica particles with a transition metal so that the silica particles are bonded to the transition metal through a covalent or coordinate bond. The method further comprises contacting the modified silica particles with an odorous compound, the transition metal providing one or more active sites for capturing the odorous compound.

Various techniques may be utilized to form the modified silica particles. In one embodiment, a salt of the transition metal is mixed with the silica particles to form a transition metal/silica particle mixture. The pH of this mixture may be selectively adjusted, such as to a pH of 7 or greater, and in some instances, to a pH of from about 9 to about 10. Such an increase in pH may have a variety of benefits. For instance, many silica sols are considered stable at a pH of greater than about 7, and particularly between a pH of 9-10. When dissolved in water, salts of transition metals are acidic (e.g., copper chloride has a pH of approximately 4.8). Thus, when such an acidic transition metal salt is mixed with a basic silica sol, the pH is lowered and the metal salt precipitates on the surface of the silica particles. This compromises the stability of the silica particles. Further, at lower pH values, the number of silanol groups present on the surface of the silica particles is reduced. Because the transition metal may bind to these silanol groups, the capacity of the particles for the transition metal is lowered at lower pH values. Thus, to ameliorate the pH-lowering affect caused by the addition of an acidic transition metal salt (e.g., copper chloride), certain embodiments of the present invention employ selective control over the pH of the silica particles during mixing with the transition metal.

The selective control over pH may be accomplished in a variety of ways. For instance, in one embodiment, urea thermal decomposition (i.e., pyrolysis) may be used to increase pH to the desired value. One advantage of using urea decomposition to control the pH of the transition metal/silica mixture is the ability to easily manipulate pH as the metal and silica are mixed together. For instance, the pyrolysis of urea produces ammonia ($NH_3$) as a byproduct. In some embodiments of the present invention, the presence of this ammonia byproduct may be used to increase the pH of the transition metal/silica mixture to the desired level. Besides urea decomposition, other techniques may also be employed to selectively adjust the pH of the transition metal/silica mixture. For instance, in one embodiment, a buffer system containing an alkali metal bicarbonate and an alkali metal carbonate may be employed. In another embodiment, a basic compound may be employed, such as sodium hydroxide, potassium hydroxide, ammonium hydroxide, and so forth.

Other techniques may also be utilized to form the modified silica particles. For instance, organofunctional silanes may be used in some embodiments to bond the transition metal to the silica particle. Example of such silanes may include, for instance, organofunctional alkoxysilanes, such as aminofunctional alkoxysilanes. The organofunctional silanes may be covalently bonded to the silica particles through the silanol groups (Si—OH) present on the surface thereof. Specifically, the silicon atom of the silane may form a covalent bond with the oxygen of the silanol group. The organofunctional group of the silane may also form a coordinate bond with the transition metal. For example, in one embodiment, copper may form a coordinate bond with different amino groups present on aminopropyltriethoxysilanes.

In accordance with another embodiment of the present invention, a substrate for reducing odor is disclosed. The substrate contains silica particles bonded to a transition metal through a covalent or coordinate bond, the transition metal providing one or more active sites for capturing an odorous compound. In one embodiment, the substrate comprises a nonwoven, woven, or paper web. In one embodiment, the substrate may be incorporated into an absorbent article. For example, the absorbent article may include at least one liquid-transmissive layer and a liquid-absorbent core, wherein the substrate forms at least a portion of the liquid-transmissive layer, the liquid-absorbent core, or combinations thereof. In addition, the absorbent article may include a liquid-transmissive liner, a liquid-transmissive surge layer, a liquid-absorbent core, and a vapor-permeable, liquid-impermeable outer cover, the substrate forming at least a portion of the liner, surge layer, absorbent core, outer cover, or combinations thereof. In another embodiment, the substrate may be incorporated into a paper product, such as a bath tissue, facial tissue, paper towel, etc., or a facemask.

Other features and aspects of the present invention are discussed in greater detail below.

DETAILED DESCRIPTION OF REPRESENTATIVE EMBODIMENTS

Definitions

As used herein, a "coordinate bond" refers to a shared pair of electrons between two atoms, wherein one atom supplies both electrons to the pair.

As used herein, a "covalent bond" refers to a shared pair of electrons between two atoms, wherein each atom supplies one electron to the pair.

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel. et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo. et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to silica particles configured to reduce various types of odors. The silica particles may possess various forms, shapes, and sizes depending upon the desired result. For instance, the silica particles may be in the shape of a sphere, crystal, rod, disk, tube, string, etc. The average size of the silica particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter.

The silica particles may have a surface area of from about 50 square meters per gram ($m^2/g$) to about 1000 $m^2/g$, in some embodiments from about 100 m 2/g to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. If desired, the silica particles may also be relatively nonporous or solid. That is, the silica particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that silica particles having such a small size and high surface area may improve the adsorption capability of the silica for many odorous compounds. Moreover, it is believed that the solid nature, i.e., low pore volume, of the silica particles may enhance the uniformity and stability of the silica, without sacrificing its odor adsorption characteristics. Commercially available examples of silica nanoparticles, such as described above, include Snowtex-C, Snowtex-O, Snowtex-PS, and Snowtex-OXS, which are available from Nissan Chemical of Houston, Tex. Snowtex-OXS particles, for instance, have a particle size of from 4 to 6 nanometers, and may be ground into a powder having a surface area of approximately 509 square meters per gram.

Silica particles, such as described above, may possess units that may or may not be joined together. Whether or not such units are joined generally depends on the conditions of polymerization. For instance, the acidification of a silicate solution may yield $Si(OH)_4$. If the pH of this solution is reduced below 7 or if a salt is added, then the units may tend to fuse together in chains and form a "silica gel." On the other hand, if the pH is kept at a neutral pH or above 7, the units may tend to separate and gradually grow to form a "silica sol." Such silica particles may generally be formed according to any of a variety of techniques well known in the art, such as dialysis, electrodialysis, peptization, acid neutralization, and ion exchange. Some examples of such techniques are described, for instance, in U.S. Pat. No. 5,100,581 to Watanabe, et al.; U.S. Pat. No. 5,196,177 to Watanabe, et al.; U.S. Pat. No. 5,230,953 to Tsugeno, et al. and U.S. Pat. No. 5,985,229 to Yamada, et al., which are incorporated herein in their entirety by reference thereto for all purposes.

In one particular embodiment, a silica sol is formed using an ion-exchange technique. For exemplary purposes only, one such ion-exchange technique will now be described in more detail. Initially, an alkali metal silicate is provided that has a molar ratio of silicon ($SiO_2$) to alkali metals ($M_2O$) of from about 0.5 to about 4.5. For instance, sodium water glass may be utilized that has a molar ratio of from about 2 to about 4. An aqueous solution of the alkali metal silicate is obtained by dissolving it in water at a concentration of, for instance, from about 2 wt. % to about 6 wt. %. The alkali metal silicate-containing aqueous solution may then be contacted with one or more ion-exchange resins. For instance, the solution may first be contacted with a strong-acid to ion-exchange all the metal ions in the aqueous solution. Examples of such strong acids include, but are not limited to, hydrochloric acid, nitric acid, sulfuric acid, and so forth. The contact may be accomplished by passing the aqueous solution through a column filled with the strong acid at a temperature of from about 0° C. to about 60° C., and in some embodiments, from about 5° C. to about 50° C. After passing through the column, the resulting silicic acid-containing aqueous solution may have a pH value of from about 2 to about 4. If desired, another strong acid may be added to the silicic acid-containing aqueous solution to convert the impurity metal components into dissociated ions. This additional strong acid may decrease the pH value of the resulting solution to less than about 2, and in some embodiments, from about 0.5 to about 1.8.

The metal ions and the anions from the strong acid may be removed from the solution by consecutive application of a strong acid (i.e., cation-exchange resin) and strong base (anion-exchange resin). Examples of suitable strong bases include, but are not limited to, sodium hydroxide, potassium hydroxide, and so forth. As a result of this consecutive application, the silicic acid-containing aqueous solution may have a pH value of from about 2 to about 5. This acidic aqueous solution may then be contacted with one or more additional strong bases to stabilize the solution at a pH value of from about 7 to about 9.

The stabilized silicic acid-containing aqueous solution is then fed to a container in which the liquid temperature is maintained at from about 70° C. to about 100° C. This process results in an increase in concentration of the silica to from about 30 wt. % to about 50 wt. %. The stable aqueous silica sol may then be consecutively contacted with a strong acid and strong base, such as described above, so that the resulting aqueous silica sol is substantially free from polyvalent metal oxides, other than silica. Finally, ammonia may be added to the aqueous sol to further increase its pH value to from about 8 to about 10.5, thereby forming a stable aqueous silica sol having a silica concentration of from about 30 wt. % to about 50 wt. %, a mean particle size of from about 10 to about 30 nanometers, and that is substantially free from any polyvalent metal oxides, other than silica.

In accordance with the present invention, the silica particles are modified with one or more transition metals. Examples of some suitable transition metals that maybe used in the present invention include, but are not limited to, scandium, titanium, vanadium, chromium, manganese, iron, cobalt, nickel, copper, zinc, silver, gold, and so forth. Single metallic, as well as dimeric, trinuclear, and cluster systems may be used. Without being limited by theory, it is believed that the transition metal provides one or more active sites for capturing and/or neutralizing an odorous compound. Further, the presence of the transition metal is also believed to help improve the Lewis acidity of the silica, thus rendering it more receptive to free electron pairs of many odorous compounds.

The transition metal may be incorporated onto the surface of the silica particles in a variety of ways. For instance, silica particles may simply be mixed with a solution containing the appropriate transition metal in the form of a salt, such as those containing a copper ion ($Cu^{+2}$), silver ion ($Ag^+$), gold ion ($Au+$ and $Au^{+3}$), iron (II) ion ($Fe^{+2}$), iron (III) ion ($Fe^{+3}$), and so forth. Such solutions are generally made by dissolving a metallic compound in a solvent resulting in free metal ions in the solution. Generally, the metal ions are drawn to and adsorbed onto the silica particles due to their electric potential differences, i.e., they form an "ionic" bond. In many instances, however, it is desired to further increase the strength of the bond formed between the metal and silica particles, e.g., to form a "coordinate" and/or "covalent bond." Although ionic bonding may still occur, the presence of coordinate or covalent bonding may have a variety of benefits, such as reducing the likelihood that any of the metal will remain free during use (e.g., after washing). Further, a strong adherence of the metal to the silica particles also optimizes odor adsorption effectiveness.

Numerous techniques may be utilized to form a stronger bond between the transition metal and silica particles. For example, silica sols are generally considered stable at a pH of greater than about 7, and particularly between a pH of 9-10. When dissolved in water, salts of transition metals are acidic (e.g., copper chloride has a pH of approximately 4.8). Thus, when such an acidic transition metal salt is mixed with a basic silica sol, the pH is lowered and the metal salt precipitates on the surface of the silica particles. This compromises the stability of the silica particles. Further, at lower pH values, the number of silanol groups present on the surface of the silica particles is reduced. Because the transition metal binds to these silanol groups, the capacity of the particles for the transition metal is lowered at lower pH values. Thus, to ameliorate the pH-lowering affect caused by the addition of an acidic transition metal salt (e.g., copper chloride), certain embodiments of the present invention employ selective control over the pH of the silica particles during mixing with the transition metal.

The selective control over pH may be accomplished using any of a variety of well-known buffering systems known in the art. One such buffering system utilizes urea thermal decomposition (i.e., pyrolysis) to increase pH to the desired value. The pyrolysis of urea is well known, and has been described in, for instance, *Study of the Urea Decomposition (Pyrolysis) Reaction and Importance to Cyanuric Acid Production*, Peter M. Shaber, et al., American Laboratory (August 1999), which is incorporated herein in its entirety by reference thereto for all purposes. For instance, to initiate the pyrolysis reaction, urea is first heated to its melting point of approximately 135° C. With continued heating to approximately 150° C., the urea is vaporized (Eq. 1) and is then decomposed into ammonia and isocyanic acid (Eq. 2). The urea also reacts with the isocyanic acid byproduct to form biuret (Eq. 3).

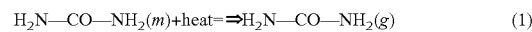
$$H_2N—CO—NH_2(m)+heat=\Rightarrow H_2N—CO—NH_2(g) \quad (1)$$

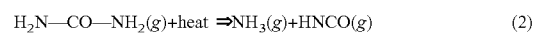
$$H_2N—CO—NH_2(g)+heat \Rightarrow NH_3(g)+HNCO(g) \quad (2)$$

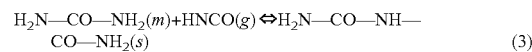
$$H_2N—CO—NH_2(m)+HNCO(g) \Leftrightarrow H_2N—CO—NH—CO—NH_2(s) \quad (3)$$

Upon further heating, e.g., to about 175° C., the biuret referenced above reacts with isocyanic acid to form cyanuric acid and ammonia (Eq. 4), as well as ammelide and water (Eq. 5).

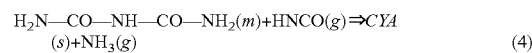
$$H_2N—CO—NH—CO—NH_2(m)+HNCO(g) \Rightarrow CYA(s)+NH_3(g) \quad (4)$$

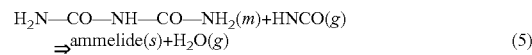
$$H_2N—CO—NH—CO—NH_2(m)+HNCO(g) \Rightarrow \text{ammelide}(s)+H_2O(g) \quad (5)$$

As the temperature is further increased, other reactions begin to occur. For instance, biuret may decompose back into urea and isocyanic acid. The urea produced is unstable at higher temperatures, and thus, will further decompose into ammonia and isocyanic acid. Urea and the byproducts of the pyrolysis reaction will continue to react and further decompose as the reaction mixture is heated.

One advantage of using urea decomposition to control the pH of the transition metal/silica mixture is the ability to easily manipulate pH as the metal and silica are mixed together. For instance, as indicated above, the pyrolysis of urea produces ammonia ($NH_3$) as a byproduct. In some embodiments of the present invention, the presence of this ammonia byproduct may be used to increase the pH of the transition metal/silica mixture to the desired level. The amount of ammonia present in the mixture may be easily controlled by selectively varying the amount of urea reactant and the temperature to which the urea is heated. For instance, higher pyrolysis temperatures generally result in a greater amount of resulting ammonia due to the greater extent to which the urea and its byproducts are decomposed.

Besides urea decomposition, other well-known buffering systems may also be employed in the present invention to increase the pH of the transition metal/silica mixture to the desired level. For instance, in one embodiment, the buffering system may use an alkali metal bicarbonate and an alkali metal carbonate in a certain molar ratio. The alkali metal cations may be, for instance, sodium and/or potassium. In one particular embodiment, the buffering system employs sodium carbonate ($Na_2CO_3$) and sodium bicarbonate ($NaHCO_3$). In other embodiments of the present invention, the buffering system may simply involve adding a certain amount of a basic compound to the mixture, such as sodium hydroxide, potassium hydroxide, ammonium hydroxide, and so forth. Regardless of the technique for increasing the pH of the transition metal/silica mixture, the present inventors have discovered that the adjustment allows stronger bonds to be formed between the transition metal and silica particles. Specifically, without intending to be limited by theory, it is believed that the transition metal is capable of forming covalent bonds with the silanol groups present on the silica particle surface. In addition, the higher pH increases the number of silanol groups available for binding and reduces salt precipitation, thereby enhancing bonding efficiency. Of course, due to the opposite charge of the transition metal and some types of silica particles, some binding via electrostatic attraction will also be present.

Apart from pH adjustment, other techniques may also be utilized to further enhance the strength of the bonds formed between the transition metal and the silica particles. For instance, coupling agents may be used to link the transition metal to the silica particle. Such coupling agents may be employed with or without the pH adjustment discussed above. For instance, in some embodiments, an organofunctional silane coupling agent may be used to link the transition metal to the silica particles. Some examples of suitable organofunctional silane coupling agents that may be used include, but are not limited to, vinyltrichlorosilane, vinyltrimethoxysilane, vinyltriethoxysilane, vinylmethyldichlorosilane, vinylmethyldimethoxysilane, vinylmethyldiethoxysilane, 5-hexenyltrimethoxysilane, 3-glycidoxypropyltrimethoxysilane, 3-glycidoxypropyltriethoxysilane, 3-glycidoxypropylmethyldimethoxysilane, 3-glycidoxypropylmethyldiethoxysilane, 3-(meth)acryloxypropyltrimethoxysilane, 3-(meth)acryloxypropyltriethoxysilane, 3-(meth)acryloxypropylmethyldimethoxysilane, 3-(meth)acryloxypropylmethyldiethoxysilane, 4-vinylphenyltrimethoxysilane, 3-(4-vinylphenyl)propyltrimethoxysilane, 4-vinylphenylmethyltrimethoxysilane, 3-aminopropyltrimethoxysilane, 3-aminopropyltriethoxysilane, 3-aminopropylmethyldimethoxysilane, 3-aminopropylmethyldiethoxysilane, 3-(2-aminoethyl)aminopropyltrimethoxysilane, 3-mercaptopropyltrimethoxysilane, 3-mercaptopropyltriethoxysilane, 3-mercaptopropylmethyld imethoxysilane, 3-mercaptopropylmethyldiethoxysilane, and partial hydrolyzates thereof. Of these coupling agents, organofunctional alkoxysilanes, and particularly aminofunctional alkoxysilanes (e.g., 3-aminopropyltriethyoxysilane), are preferred.

Generally speaking, the silane coupling agents may be covalently linked to the silica particles through the silanol groups (Si—OH) present on the surface thereof. Specifically, the silicon atom of the silane coupling agent may form a covalent bond with the oxygen of the silanol group. Once the silane coupling agent is covalently linked to the silica particles, the organofunctional group may form a coordinate bond with the transition metal. For example, in one embodiment, copper may form a coordinate bond with different amino groups present on aminopropyltriethoxysilane coupling agents. An example of this reaction mechanism is set forth below:

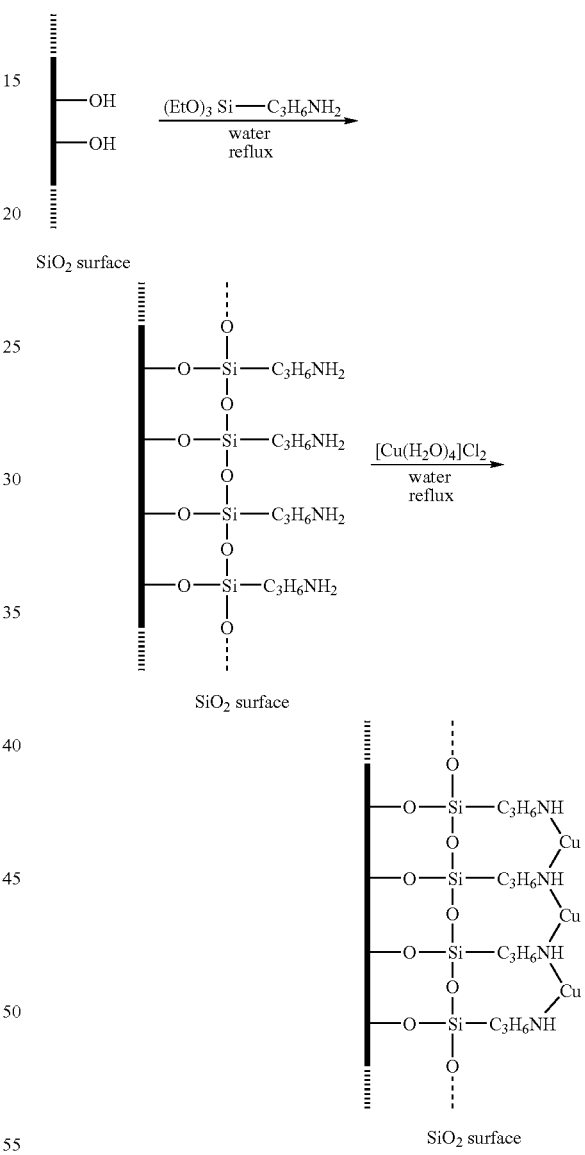

The present inventors have discovered that the coordinate complex formed between the transition metal and silane coupling agent is strong, and thus, reduces the likelihood that any free metal will be present during use (e.g., after washing).

The transition metal present on the surface of the silica particle of the present invention is believed to provide one or more active sites for capturing and/or neutralizing odorous compounds. The active sites may be free, or may be weak enough so that they are replaced by an odorous molecule when contacted therewith. In addition, the particles still have the large surface area that is useful in absorbing other odorous compounds. For example, the silica particles of the present invention may be used in various applications to remove odorous compounds, such as mercaptans (e.g., ethyl mercaptan), ammonia, amines (e.g., trimethylamine (TMA), triethylamine (TEA), etc.), sulfides (e.g., hydrogen sulfide, dimethyl disulfide (DMDS), etc.), ketones (e.g., 2-butanone, 2-pentanone, 4-heptanone, etc.) carboxylic acids (e.g., isovaleric acid, acetic acid, propionic acid, etc.), aldehydes, terpenoids, hexanol, heptanal, pyridine, and combinations thereof.

If desired, more than one type of transition metal may be bound to a silica particle. This has an advantage in that certain metals may be better at removing specific odorous compounds than other metals. Likewise, different types of modified silica particles may be used in combination for effective removal of various odorous compounds. In one embodiment, for instance, copper-modified silica particles are used in combination with manganese-modified silica particles By using two different modified particles in combination, numerous odorous compounds may be more effectively removed. For example, the copper-modified particle may be more effective in removing sulfur and amine odors, while the manganese-modified particle may be more effective in removing carboxylic acids.

The ratio of the transition metal to the silica particles may be selectively varied to achieve the desired results. In most embodiments, for example, the ratio of the transition metal to the silica particles is at least about 10:1, in some embodiments at least about 50:1, and in some embodiments, at least about 100:1. Generally speaking, the order in which the particles, buffer and/or coupling agent, and transition metal are mixed may be varied as desired. In some instances, the order of mixing may actually affect the characteristics of the modified silica particles. For instance, in one embodiment, the buffer and/or coupling agent is first added to the silica particles, and then the transition metal is added.

If desired, the modified silica particles of the present invention may be applied to a substrate. The substrate may provide an increased surface area to facilitate the adsorption of odorous compounds by the particles. In addition, the substrate may also serve other purposes, such as water absorption. Any of a variety of different substrates may be incorporated with the modified silica particles in accordance with the present invention. For instance, nonwoven fabrics, woven fabrics, knit fabrics, wet-strength paper, film, foams, etc., may be applied with the particles. When utilized, the nonwoven fabrics may include, but are not limited to, spunbonded webs (apertured or non-apertured), meltblown webs, bonded carded webs, air-laid webs, coform webs, hydraulically entangled webs, and so forth.

In some embodiments, for example, the modified silica particles may be utilized in a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter (gsm), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-1 g". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized. Some suitable synthetic fibers can include, but are not limited to, rayon fibers, ethylene vinyl alcohol copolymer fibers, polyolefin fibers, polyesters, and so forth.

If desired, the substrate may form all or a portion of an absorbent article. In one embodiment, for instance, the absorbent article includes a liquid-transmissive bodyside liner, a liquid-transmissive surge layer below the bodyside liner, a liquid-absorbent core below the surge layer, and a moisture vapor permeable, liquid impermeable outer cover below the absorbent core. A substrate treated with the modified silica particles of the present invention may be employed as any one or more of the liquid transmissive (non-retentive) and absorbent layers. An absorbent core of the absorbent article, for instance, may be formed from an absorbent nonwoven web that includes a matrix of hydrophilic fibers. In one embodiment, the absorbent web may contain a matrix of cellulosic fluff fibers. One type of fluff that may be used in the present invention is identified with the trade designation CR1654, available from U.S. Alliance, Childersburg, Ala., U.S.A., and is a bleached, highly absorbent sulfate wood pulp containing primarily soft wood fibers. In another embodiment, the absorbent nonwoven web may contain a hydoentangled web. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

Another type of suitable absorbent nonwoven web is a coform material, which is typically a blend of cellulose fibers and meltblown fibers. The term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and so forth. Some examples of such coform materials are disclosed in U.S. Pat. No. 4,100,324 to Anderson, et al.; U.S. Pat. No. 5,284,703 to Everhart. et al.; and U.S. Pat. No. 5,350,624 to Georger, et al.; which are incorporated herein in their entirety by reference thereto for all purposes.

If desired, the absorbent nonwoven web may also contain a superabsorbent material. Superabsorbents have the ability to absorb a great amount of fluid in relation to their own weight. Typical superabsorbents used in sanitary napkins may absorb anywhere from about 5 to about 60 times their weight in blood. Superabsorbent materials are produced in a wide variety of forms including, but not limited to, particles, fibers and flakes. Superabsorbents having a high mechanical stability in the swollen state, an ability to rapidly absorb fluid, and those having a strong liquid binding capacity, typically perform well in absorbent articles. Hydroxyfunctional polymers have been found to be good superabsorbents for this application. For example, a hydrogel-forming polymer, such as a partially neutralized cross-linked copolymer of polyacrylic acid and polyvinyl alcohol, may be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents may be obtained from Dow Chemical and Stockhausen, Inc., among others. This superabsorbent is a partially neutralized salt of cross-linked copolymer of polyacrylic acid and polyvinyl alcohol having an absorbency under load value above about 25. Some suitable superabsorbents are described in U.S. Pat. No. 4,798,603 to Meyers, et al., Re. 32,649 to Brandt, et al. and U.S. Pat. No. 4,467,012 to Pedersen, et al., U.S. Pat. No. 4,604,313 and U.S. Pat. No. 4,655,757 to McFarland, et al., U.S. Pat. No. 6,387,495 to Reeves, et al., as well as in published European Patent Application 0,339,461 to Kellenberger.

As indicated above, the modified silica particles may also be applied to a liquid transmissive layer of the absorbent article, such as the bodyside liner or surge layer. Such liquid transmissive layers are typically intended to transmit liquid quickly, and thus generally do not retain or absorb significant quantities of aqueous liquid. Materials that transmit liquid in such a manner include, but are not limited to, thermoplastic spunbonded webs, meltblown webs, bonded carded webs, air laid webs, and so forth. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$-$C_{20}$ alpha-olefin, terpolymers of ethylene with propylene and a $C_4$-$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing.

The amount of the modified silica particles present on the substrate may vary depending on the nature of the substrate and its intended application. In some embodiments, for example, the dry, solids add-on level is from about 0.001% to about 20%, in some embodiments from about 0.01% to about 10%, and in some embodiments, from about 0.1% to about 4%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum absorbency or other characteristics of the substrate, while higher add-on levels may provide optimum odor reduction.

The modified silica particles may be applied to a substrate using any of a variety of well-known application techniques. Suitable techniques for applying the composition to a substrate include printing, dipping, spraying, melt extruding, solvent coating, powder coating, and so forth. The modified silica particles may be incorporated within the matrix of the substrate and/or applied to the surface thereof. For example, in one embodiment, the modified silica particles are coated onto one or more surfaces of the substrate. When coated onto the substrate, the resulting thickness of the coating may be minimal so that it is almost invisible to the naked eye. For instance, the thickness of the coating may be less than about 2 microns, in some embodiments from about 2 to about 500 nanometers, and in some embodiments, from about 20 to about 200 nanometers.

The percent coverage of the modified silica particles on the surface may be selected to achieve the desired odor reduction. Typically, the percent coverage is greater than about 50%, in some embodiments greater than about 80%, and in some embodiments, approximately 100% of the area of a given surface. The present inventors have discovered that, even when applied uniformly (e.g., about 100% coverage) onto a surface of the substrate, the resulting substrate may still remain porous. Specifically, without intending to be limited by theory, it is believed that the small size of the modified silica particles limits their ability to block the pores of the substrate. Thus, in some instances, a substrate containing the particle coating may remain porous to provide a variety of benefits. For instance, the porosity of the coated substrate may enable it to still be used in application where liquid permeability is required, such as in absorbent articles. Also, the porosity of the coated substrate allows gaseous odorous compounds to flow therethrough, exposing the underside of the nanoparticles (surface of particles facing the substrate) to the odorous compound. In this manner, the entire surface area of the particles is more effectively utilized for reducing odor. In most embodiments, the coated substrate exhibits a porosity such that about 20 cubic feet of air or greater may flow through 1 square foot of the substrate in 1 minute under an air pressure differential of 125 Pascals (0.5 inches of water). In other words, such a substrate is said to have an air permeability of about 20 cubic feet per minute (cfm) or greater. In some embodiments, the air permeability ranges from about 20 cfm to about 500 cfm, in some embodiments from about 50 cfm to about 400 cfm, and in some embodiments, from about 75 cfm to about 300 cfm, under an air pressure differential of 125 Pascals. Air permeability (volumetric air flow per square foot of material under an air pressure differential of 125 Pascals) may be measured in a variety of ways. For example, "Frazier Air Permeability" is determined according to Federal Test Standard 191A, Method 5450 with a Frazier Air Permeability Tester (Frazier Precision Instrument Co., Gaithersburg, Md.), and is reported as an average of 3 sample readings.

The modified silica particles of the present invention are versatile and may also be used with other types of articles of manufacture. For instance, the modified silica particles may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the silica particles of the present invention may be utilized as a filtration layer of the facemask. Filtration layers, such as meltblown nonwoven webs, spunbond nonwoven webs, and laminates thereof, are well known in the art.

In another embodiment, the modified silica particles may be applied to walls, wallpaper, glass, toilets, and/or countertops. For instance, the modified silica particles may be used in a restroom facility. Other uses include, without limitation, refrigerator mats and fabric softener sheets.

The modified silica particles may also be applied to water treatment systems for removing sulphurous compounds from well water or in toilet tanks to reduce the odors resulting from urine. The modified silica particles may also be used in liquid detergents and household cleaners to remove odors. In another embodiment, the modified silica particles are used as aerosol odor neutralizers/deodorants. The modified silica particles are packaged with a propellant that allows spraying the modified silica particles into the air for removal of gases and odorous compounds. The modified silica particles may be used in a household air freshener or be used in combination with a mist emitted from a vaporizer or humidifier.

The effectiveness of the modified silica particles of the present invention may be measured in a variety of ways. For example, the percent of an odorous compound adsorbed by the modified silica particles may be determined in accordance with the headspace gas chromatography test set forth herein. In some embodiments, for instance, the modified silica particles of the present invention are capable of adsorbing at least about 25%, in some embodiments at least about 45%, and in some embodiments, at least about 65% of a particular odorous compound. The effectiveness of the modified silica particles in removing odors may also be measured in terms of "Relative Adsorption Efficiency", which is also determined using headspace gas chromatography and measured in terms of milligrams of odor adsorbed per gram of modified silica particle. It should be recognized that the surface chemistry of any one type of modified silica particle may not be suitable to reduce all types of odors, and that low adsorption of one or more odorous compounds may be compensated by good adsorption of other odorous compounds.

The present invention may be better understood with reference to the following examples.

Test Methods

Quantitative and qualitative odor tests were used in the Examples.

Quantitative odor adsorption was determined in the Examples using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

Operating Parameters for the Headspace Gas Chromatography Device.
Headspace Parameters

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 5 milligrams of the modified silica particles in a 20-cubic centimeter headspace vial. Using a syringe, an aliquot of the odorous compound was also placed in the vial. Testing was done with 839 micrograms of ethyl mercaptan (1 microliter), 804 micrograms (1 microliter) of isovaleraldehyde, and 726 micrograms (1 microliter) of triethylamine (TEA). Each sample was tested in triplicate. The vial was then sealed with a cap and a septum and placed in the headspace gas chromatography oven at 37° C. After two (2) hours, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial.

Qualitative odor reduction was also assessed against common odors, such as garlic, cigarette and urine.

EXAMPLE 1

The ability to form modified silica particles was demonstrated. The silica particles were Snowtex-PSSO, which are colloidal silica nanoparticles commercially available from Nissan Chemical America of Houston, Tex. The particles have an average particle size of between 10 to 20 nanometers and a surface area between 180 to 240 square meters per gram. The silica particles were modified with a transition metal as follows. Initially, 3-aminopropyltriethyoxysilane (5 millimoles, 1.17 milliliters) was dissolved in 50 milliliters of water and transferred to a 500-milliliter round bottom flask. A solution of the Snowtex-PSSO particles (200 milliliters of a 2.6 wt. % solution) was slowly added to the silane solution while vigorously stirring. The resultant reactant solution was allowed to reflux for 48 hours, and then cooled to room temperature. Once the reactant solution was cooled, a solution of copper chloride ($CuCl_2$) (5 millimoles, 672 micrograms) in 50 milliliters of water was slowly added to the reactant solution and allowed to reflux for 48 hours. The solution was allowed to cool to room temperature, and stirred at ambient conditions for another 48 hours. The solvent was then removed en vacuo. The resulting product, which was pale blue, was washed extensively with acetone, water, and acetone once again. The product was dried overnight in a vacuum oven.

EXAMPLE 2

The effectiveness of the modified silica particles to adsorb odorous compounds was demonstrated. The modified particles of Example 1 were tested for odor adsorption as described above. In addition, silica particles mixed with copper chloride without the use of a silane coupling agent were also tested at a copper-to-silica ratio of 60:1. These samples were formed from Snowtex-PSSO, Snowtex-C, Snowtex-O, and Snowtex-AK silica nanoparticles, which are colloidal silica nanoparticles commercially available from Nissan Chemical America of Houston, Tex. The particles have an average particle size of between 10 to 20 nanometers and a surface area between 180 to 240 square meters per gram. For comparative purposes, activated carbon (obtained from Aldrich) and RX 4483, which is precipitated calcium carbonate obtained from Specialty Minerals of New York, N.Y., were also tested.

The results are shown below in Table 2 in terms of milligrams of the odorous compound removed per gram of sample, i.e., relative adsorption efficiency.

TABLE 2

Removal of Ethyl Mercaptan

| Sample | Relative Adsorption Efficiency (mg odor removed/g sample) |
| --- | --- |
| Copper-Modified Snowtex-PSSO from Ex. 1 | 26.393 |
| Copper/Snowtex-C Mixture | 13.413 |
| Copper/Snowtex-O Mixture | 21.139 |
| Copper/Snowtex-PSSO Mixture | 13.906 |
| Copper/Snowtex-AK Mixture | 11.763 |
| RX 4483 | 5.546 |
| Activated Carbon | 22.677 |

As indicated, the present invention provided excellent adsorption of ethyl mercaptan.

EXAMPLE 3

The ability to form modified silica particles was demonstrated. The silica particles were Snowtex-C, which are colloidal silica nanoparticles commercially available from Nissan Chemical America of Houston, Tex. The particles have an average particle size of between 10 to 20 nanometers and a surface area between 180 to 240 square meters per gram. A solution of the Snowtex-C particles (26.2 grams of a 20 wt. % solution, 8.47 micromoles of silica) was applied with a solution of copper nitrate ($Cu(NO_3)_2$) (317 milligrams, 1.69 millimoles) in 40 milliliters of water. A solution of urea (102 milligrams, 1.69 millimoles) in 160 milliliters of water was also applied to the mixture. The resultant reactant solution was allowed to reflux for 24 hours at 105° C., and then cooled to room temperature. Once the reactant solution was cooled, the product was collected by centrifugation and washed extensively with portions of water and acetone. The product was dried overnight en vacuo.

EXAMPLE 4

The ability to form modified silica particles was demonstrated. The silica particles were Snowtex-C nanoparticles. A solution of the Snowtex-C particles (26.2 grams of a 20 wt. % solution, 8.47 micromoles of silica) was applied with a solution of copper nitrate ($Cu(NO_3)_2$) (317 milligrams, 1.69 millimoles) in 40 milliliters of water. A solution of ammonium hydroxide ($NH_4OH$) (138 milligrams, 8.132 millimoles) in 160 milliliters of water was also applied to the mixture. The resultant reactant solution was allowed to reflux for 24 hours at 105° C., and then cooled to room temperature. Once the reactant solution was cooled, the product was collected by centrifugation and washed extensively with portions of water and acetone. The product was dried overnight en vacuo.

EXAMPLE 5

The ability to form modified silica particles was demonstrated. The silica particles were Snowtex-PSSO nanoparticles. A solution of the Snowtex-PSSO particles (27.99 grams of a 20 wt. % solution, 4.23 micromoles of silica) was applied with a solution of copper nitrate ($Cu(NO_3)_2$) (403 milligrams, 2 millimoles) in 40 milliliters of water. A $Na_2CO_3/NaHCO_3$ buffer (pH of 9) was also applied to the mixture. The resultant reactant solution was allowed to reflux for 24 hours at 105° C., and then cooled to room temperature. Once the reactant solution was cooled, the product was collected by centrifugation and washed extensively with portions of water and acetone. The product was dried overnight en vacuo.

EXAMPLE 6

The effectiveness of the modified silica particles of Examples 1 and 3-4 to adsorb odorous compounds was demonstrated. In addition, silica particles mixed with copper chloride without the use of a pH adjustment or a silane coupling agent were also tested at a copper-to-silica ratio of 60:1. These samples were formed from Snowtex-PSSO and Snowtex-C. The results are shown below in Table 3 in terms of milligrams of the odorous compound removed per gram of sample, i.e., relative adsorption efficiency.

TABLE 3

Removal of Ethyl Mercaptan

| Sample | Relative Adsorption Efficiency (mg odor removed/g sample) |
| --- | --- |
| Copper-Modified Snowtex-PSSO from Ex. 1 | 37.730 |
| Copper-Modified Snowtex-C from Ex. 3 | 101.325 |
| Copper-Modified Snowtex-C from Ex. 4 | 87.583 |
| Copper/Snowtex-C Mixture | 27.788 |
| Copper/Snowtex-PSSO Mixture | 8.037 |

As indicated, the present invention provided excellent adsorption of ethyl mercaptan.

EXAMPLE 7

The effectiveness of the modified silica particles of Example 1 to adsorb various odorous compounds was again demonstrated. The results are shown below in Table 4 in terms of milligrams of the odorous compound removed per gram of sample, i.e., relative adsorption efficiency.

TABLE 4

Removal of Ethyl Mercaptan, Isoveraldehyde, and Triethylamine

| Sample | Relative Adsorption Efficiency of Ethyl Mercaptan (mg odor removed/g sample) | Relative Adsorption Efficiency of Isoveraldehyde (mg odor removed/g sample) | Relative Adsorption Efficiency of TEA (mg odor removed/g sample) |
|---|---|---|---|
| Copper-Modified Snowtex-PSSO from Ex. 1 | 84.81 | 65.17 | 52.21 |

EXAMPLE 8

The potential to modify silica particles with an insoluble layer of copper hydroxide was demonstrated. The silica particles were Snowtex-OXS, which are colloidal silica nanoparticles commercially available from Nissan Chemical America of Houston, Tex. The particles have an average particle size of between 4 to 6 nanometers and a surface area between 180 to 240 square meters per gram. A solution of the Snowtex-OXS particles (10 wt. % solution) was initially adjusted to pH of 8.7, and then a solution of 1 Molar copper chloride was added with high shear mixing (10,000 rpm). The pH, Zeta potential and particle size were all monitored during addition of the copper salt. When a positive Zeta Potential was obtained, the addition of copper salt was stopped. A control sample of copper hydroxide suspension was also prepared in a similar manner. The results are shown below in Table 5.

TABLE 5

Properties of Samples

| Sample | pH | Zeta Potential mV | Particle Size (nm) | Surface Area (m²/g) |
|---|---|---|---|---|
| Snowtex-OXS | 8.7 | −55 | 9 | 509 |
| Snowtex-OXS/Cu(OH)$_2$ | 8.6 | 38 | 43 | 508 |
| Cu(OH)$_2$ | 8.5 | −8 | 36,735 | Not Determined |

The above results clearly show a successful coating of the copper hydroxide onto the silica surface resulting in a positively charged particle having a small size (diameter). In contrast, the copper hydroxide formed in solution by itself formed large particles and remained negatively charged.

After formation, the water was removed from the copper hydroxide modified silica particle suspension under reduced pressure on a rotary evaporator to leave a dry powder. This powder was washed with deionized water and filtered on a Buchner funnel three times before drying in a convection oven at 100° C. The surface area of a sample of the powder was determined by BET analysis (Micromeritics, Norcross, Ga.). The coating of copper hydroxide did not have an impact on the final surface area of the dried powder.

To determine the potential for urine odor reduction, 10 milligrams of the dried powder were placed in 12 Poise® pads (available from Kimberly-Clark) on the super absorbent/fluff pledget and then re-wrapped in the tissue wrap. The pads were then insulted with 60 milliliters of pooled female urine and incubated for 24 hours in Mason jars (1 quart) with lids. 12 women panelists ranked the pads in order of most to least urine odor intensity. Untreated Poise® and "Serenity Night & Day" pads (available from SCA Hygiene Products) were used as controls. The copper hydroxide modified silica nanoparticles powder (Snowtex-OXS-Cu(OH)$_2$) had the least urine odor of the samples. The good odor absorption of urine is believed to be due to the high surface of the nanoparticles combined with the effectiveness of copper in adsorbing amine and sulfur compounds.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents tereto.

What is claimed is:

1. A method for reducing odor, said method comprising:
   mixing the salt of a transition metal with silica particles to form a transition metal/silica particle mixture;
   selectively adjusting the pH of said mixture to 7 or greater so that modified silica particles are formed that contain said silica particles bonded with said transition metal, wherein the mole ratio of the transition metal to the silica particles is at least about 10:1; and
   contacting said modified silica particles with an odorous compound, said transition metal providing one or more active sites for capturing said odorous compound.

2. A method as defined in claim 1, wherein said silica particles have an average size of less than about 100 nanometers.

3. A method as defined in claim 1, wherein said transition metal is selected from the group consisting of scandium, titanium, vanadium, chromium, manganese, iron, cobalt, nickel, copper, zinc, silver, gold, and combinations thereof.

4. A method as defined in claim 1, wherein said salt comprises a copper ion ($Cu^{+2}$), silver ion ($Ag^+$), gold ion ($Au^+$ and $Au^{+3}$), iron (II) ion ($Fe^{+2}$), iron (III) ion ($Fe^{+3}$), or combinations thereof.

5. A method as defined in claim 1 wherein said pH is selectively adjusted through a urea pyrolysis reaction.

6. A method as defined in claim 1, wherein said pH is selectively adjusted by adding an alkali metal carbonate, an alkali metal bicarbonate, or combinations thereof, to said mixture.

7. A method as defined in claim 1, wherein said pH is selectively adjusted by adding a basic compound to said mixture.

8. A method as defined in claim 1, wherein said odorous compound is selected from the group consisting of mercaptans, ammonia, amines, sulfides, ketones, carboxylic acids, aldehydes, terpenoids, hexanol, heptanal, pyridine, and combinations thereof.

9. A method for reducing odor, said method comprising:
   coupling a transition metal to a surface of silica particles with an organofunctional silane so that modified silica particles are formed that contain said silica particles bonded with said transition metal, wherein the mole ratio of the transition metal to the silica particles is at least about 10:1; and
   contacting said modified silica particles with an odorous compound, said transition metal providing one or more active sites for capturing said odorous compound.

10. A method as defined in claim 9, wherein said silica particles have an average size of less than about 100 nanometers.

11. A method as defined in claim 9, wherein said transition metal is selected from the group consisting of scandium, titanium, vanadium, chromium, manganese, iron, cobalt, nickel, copper, zinc, silver, gold, and combinations thereof.

12. A method as defined in claim 9, wherein said organofunctional silane comprises an alkoxysilane.

13. A method as defined in claim 9, wherein said organofunctional silane comprises an aminofunctional alkoxysilane.

14. A method as defined in claim 9, wherein said organofunctional silane forms a covalent bond with silanol groups present on said surface of said silica particles.

15. A method as defined in claim 14, wherein said transition metal forms a coordinate bond with said organofunctional silane.

16. A method as defined in claim 9, wherein said odorous compound is selected from the group consisting of mercaptans, ammonia, amines, sulfides, ketones, carboxylic acids, aldehydes, terpenoids, hexanol, heptanal, pyridine, and combinations thereof.

17. A method as defined in claim 1, wherein said silica particles have an average size of less than about 500 microns.

18. A method as defined in claim 1, wherein said silica particles have an average size of from about 4 to about 20 nanometers.

19. A method as defined in claim 1, wherein said silica particles have a surface area of from about 50 to about 1000 square meters per gram.

20. A method as defined in claim 1, wherein said silica particles have a pore volume of less than about 0.5 milliliters per gram.

21. A method as defined in claim 1, wherein said pH is selectively adjusted to a pH of from about 9 to about 10.

22. A method as defined in claim 7, wherein said basic compound is selected from the group consisting of sodium hydroxide, potassium hydroxide, ammonium hydroxide, and combinations thereof.

23. A method as defined in claim 1, further comprising applying said modified silica particles to a substrate.

24. A method as defined in claim 23, wherein said substrate comprises a nonwoven, woven, or paper web.

25. A method as defined in claim 1, wherein the mole ratio of the transition metal to the silica particles is at least about 50:1.

26. A method as defined in claim 1, wherein said silica particles are spherical.

27. A method as defined in claim 9, wherein said silica particles have an average size of less than about 500 microns.

28. A method as defined in claim 9, wherein said silica particles have an average size of from about 4 to about 20 nanometers.

29. A method as defined in claim 9, wherein said silica particles have a surface area of from about 50 to about 1000 square meters per gram.

30. A method as defined in claim 9, wherein said silica particles have a pore volume of less than about 0.5 milliliters per gram.

31. A method as defined in claim 9, further comprising applying said modified silica particles to a substrate.

32. A method as defined in claim 31, wherein said substrate comprises a nonwoven, woven, or paper web.

33. A method as defined in claim 9, wherein said silica particles are spherical.

34. A method as defined in claim 9, wherein the mole ratio of the transition metal to the silica particles is at least about 50:1.

35. A method as defined in claim 1, wherein the mole ratio of the transition metal to the silica particles is at least about 100:1.

36. A method as defined in claim 9, wherein the mole ratio of the transition metal to the silica particles is at least about 100:1.

* * * * *